(12) United States Patent
Yamasaki et al.

(10) Patent No.: US 7,449,154 B2
(45) Date of Patent: Nov. 11, 2008

(54) CHEMICAL-CONTAINING FORMED MATERIAL OF TYPE OF HEATING OF WHOLE THE MATERIAL, CONTAINER FOR HOLDING CHEMICAL-CONTAINING FORMED MATERIAL, DEVICE FOR HEATING AND TRANSPIRING CHEMICAL AND INDICATOR FOR CHEMICAL TO BE HEATED AND VAPORIZED

(75) Inventors: Satoshi Yamasaki, Hatsukaichi (JP);
Kazunori Yamamoto, Hatsukaichi (JP);
Tomoko Ishizuka, Hiroshima (JP)

(73) Assignee: Fumakilla Limited, Tokyo (JP)

( * ) Notice: Subject to any disclaimer, the term of this patent is extended or adjusted under 35 U.S.C. 154(b) by 861 days.

(21) Appl. No.: 10/433,519

(22) PCT Filed: Sep. 6, 2001

(86) PCT No.: PCT/JP01/07728

§ 371 (c)(1),
(2), (4) Date: Jun. 2, 2003

(87) PCT Pub. No.: WO02/060254

PCT Pub. Date: Aug. 8, 2002

(65) Prior Publication Data

US 2004/0045495 A1    Mar. 11, 2004

(30) Foreign Application Priority Data

Jan. 29, 2001   (JP) .............................. 2001-020007
Jan. 29, 2001   (JP) .............................. 2001-020460
Jun. 29, 2001   (JP) .............................. 2001-199091

(51) Int. Cl.
*A62B 7/08* (2006.01)

(52) U.S. Cl. ........................ 422/125; 422/123; 422/124; 239/34; 239/35; 239/60

(58) Field of Classification Search ................. 422/122, 422/123, 124, 125, 55–58, 119; 261/141, 261/142, 24, 26; 239/34, 35, 57, 60, 128, 239/135
See application file for complete search history.

(56) References Cited

U.S. PATENT DOCUMENTS 5,575,992 A * 11/1996 Kunze ........................ 424/76.4

(Continued)

FOREIGN PATENT DOCUMENTS

JP            01-141974 A      6/1989

(Continued)

OTHER PUBLICATIONS

English translation of International Preliminary Examination Report issued in International Application No. PCT/JP01/07728, filed Sep. 6, 2001, on which the present U.S. National Phase application is based.

*Primary Examiner*—Jill Warden
*Assistant Examiner*—Dwayne K Handy
(74) *Attorney, Agent, or Firm*—Frishauf, Holtz, Goodman & Chick, P.C.

(57) ABSTRACT

Disclosed are a chemical carrier body capable of volatilizing a chemical stably for an extended period of time, a receptacle for retaining the chemical carrier body, an indicator adapted for displaying a degree of consumption of a chemical contained in the chemical carrier body, and a chemical heating, volatilizing apparatus adapted for heating the chemical carrier body.

The chemical carrier body retaining receptacle is provided with at least one vent hole and has its inner surface spaced from the carrier body by a distance of 1 to 10 mm.

The indicator has a mark gradually disappearing and a mark gradually appearing with a lapse of time of heating.

The chemical heating, volatilizing apparatus has a heater element that is lager in size than the bottom surface of the chemical carrier body retaining receptacle and whose heat releasing surface is inclined at an angle of 0 to 70 degrees with respect to the plane on which the apparatus is placed.

18 Claims, 12 Drawing Sheets

U.S. PATENT DOCUMENTS

| | | | |
|---|---|---|---|
| 5,887,118 A * | 3/1999 | Huffman et al. | 392/390 |
| 5,928,605 A * | 7/1999 | Bonnema et al. | 422/5 |
| 6,085,026 A * | 7/2000 | Hammons et al. | 392/390 |
| 6,154,607 A * | 11/2000 | Flashinski et al. | 392/390 |
| 6,374,044 B1 * | 4/2002 | Freidel | 392/390 |
| 6,452,873 B1 * | 9/2002 | Holt et al. | 368/327 |
| 6,581,915 B2 * | 6/2003 | Bartsch et al. | 261/26 |
| 6,783,117 B2 * | 8/2004 | Wohrle | 261/26 |

FOREIGN PATENT DOCUMENTS

| | | |
|---|---|---|
| JP | 03-147731 A | 6/1991 |
| JP | 05-017307 A | 1/1993 |
| JP | 05-194103 A | 8/1993 |
| JP | 06-018676 A | 1/1994 |
| JP | 06-192007 A | 7/1994 |
| JP | 06-192008 A | 7/1994 |
| JP | 07-089806 A | 4/1995 |
| JP | 07-260955 A | 10/1995 |

* cited by examiner (a) START POINT (b)

(c)

(d) END POINT

CHEMICAL-CONTAINING FORMED MATERIAL OF TYPE OF HEATING OF WHOLE THE MATERIAL, CONTAINER FOR HOLDING CHEMICAL-CONTAINING FORMED MATERIAL, DEVICE FOR HEATING AND TRANSPIRING CHEMICAL AND INDICATOR FOR CHEMICAL TO BE HEATED AND VAPORIZED

This application is a U.S. National Phase Application under 35 USC 371 of International Application PCT/JP01/07728 filed Sep. 6, 2001.

TECHNICAL FIELD

The present invention relates to a whole heated, chemical containing body or a chemical carrier body adapted to be heated in whole for volatilization of a chemical contained therein, a chemical containing body retaining receptacle for accommodating such a chemical carrier body therein, and a chemical heating, volatilizing apparatus for heating such a chemical containing body retaining receptacle therein to cause a chemical to volatilize from its carrier body, as well as an indicator for such a heat volatilizing chemical.

BACKGROUND ART

A liquid type chemical heating, volatilizing apparatus has been known that is serviceable for a long time period, e.g., 12 hours or more.

Such a liquid type chemical heating, volatilizing apparatus makes use of a liquid chemical formed by dissolving a chemical in a solvent. In the apparatus, the liquid chemical is drawn up and partially heated (a system of this type hereinafter referred to as "a partially heated system") to cause the chemical to volatilize.

Such a partially heated system has an advantage in the ability to keep the liquid chemical constantly refreshed and hence in the easiness to preserve the chemical's efficacy stably for long.

However, the need for the section where the liquid chemical with the chemical dissolved in the solvent is retained, i.e., a chemical storage container and the section where it is heated to be held separately each from other and the need for the liquid chemical drawn up to be lower in viscosity, hence for the liquid chemical in its storage container to be thinner in chemical's concentration and thus to be larger in volume are entailed, which give the apparatus a disadvantage that it must on the whole be relatively large in size.

The partially heated system further requires the chemical in the liquid chemical to be held at a fixed density in order to cause the chemical to volatilize stably. Otherwise, not only is the chemical discharged but also the solvent must be emitted into the atmosphere, possibly affecting the environment adversely.

As an alternative apparatus, a whole heated system has also been known in which a chemical containing or carrier body is heated on its entirety by a heater element to cause the chemical contained therein to volatilize.

In such a whole heated system, the chemical retaining section and its heating section are naturally united together, making it possible to make up the apparatus in a compact design.

This also makes it unnecessary to hold the chemical in a constant density as required in the partially heated system. With no additional emission of such as solvent, therefore, the whole heated system is by nature pro-environmental.

The known, whole heated, chemical volatilizing apparatus using the conventional, whole heated, chemical containing body, however, makes it extremely difficult to cause the chemical to volatilize stably for a long time period.

That is, the conventional whole heated, chemical containing body used in the whole heated, chemical volatilizing apparatus so far made has had a thickness of around 2 mm, which has so limited its chemical content that it cannot keep the chemical volatilizing for long.

Making the plane geometry of the chemical containing body larger in size may make its chemical content larger in amount. But, the household use of the chemical heating, volatilizing apparatus imposes a limitation on its plane geometrical size from a requirement for its portability and from a limitation such as of the space of its set place. Also, requirements based on power consumption by the heater element impose a limitation on its plane geometrical size and in turn that of the chemical containing body.

A chemical heating, volatilizing apparatus has also been known that has an indicator set on its chemical heating, volatilizing vessel, in which the indicator displays a start and an end point of the chemical, thereby conveying to the user the depletion of the effective ingredient in the chemical.

Such an indicator makes use of a material that when heated changes its color, e.g., a thermally color changing lamination as disclosed in JP55-152059 A. In the indicator proposed in this patent literature, the thermally color changing lamination is heated by heat emitted from the heater element while the chemical is heated to volatilize thereby to cause the lamination to change its appearance from a colorless to a colored appearance, and the completion of the color change is made coincident with the depletion of the effective ingredient of the chemical, i.e., with its end point.

Indicators have also been proposed in which color change is used to display the characters "END", or a sheet in its entirety discolors to display the end point.

However, merely presenting a change from a colorless to a colored appearance or from one color to another color makes it obscure and hard to discriminate the end point, and thus makes it difficult for the user to notice the depletion of the effective ingredient of the chemical.

Accordingly, it is an object of the present invention to provide a whole heated, chemical containing or carrier body that can volatilize a chemical stably for an extended time period.

It is also an object of the present invention to provide a chemical containing or carrier body retaining receptacle whereby vapor of the chemical can pass smoothly between an inner surface of the receptacle and the chemical containing body and can diffuse through a vent hole into its outside.

It is also an object of the present invention to provide a chemical heating, volatilizing apparatus that can be made in a compact design.

It is also an object of the present invention to provide an indicator for a heat volatilizing chemical that enables the user to clearly recognize the depletion of the effective ingredient of the chemical.

DISCLOSURE OF THE INVENTION

Zealous and extensive investigations and experiments conducted by the present inventors as regards the size of a heater element, its heating temperature, conditions of the volatilization of a chemical from its carrier body and other parameters have led them to discovery of a whole heated, chemical containing or carrier body that is capable of volatilizing the chemical stably for an extended time period, more than 12 hours.

A whole heated, chemical containing or carrier body is provided in accordance with the present invention, which is characterized in that it is so configured that it has a thickness of 3 mm or more and its percentage loss of heat L that is derived from its heating temperature h and its lowest temperature t by the formula: $L=[(h-t)/h]\times 100$ is 70% or less.

The whole heated, chemical containing or carrier body so configured in accordance with the present invention has been found to permit the chemical to volatilize stably for an extended time period.

The body for containing a chemical may be made of at least one material selected from the group that consists of a caked body and/or a sintered body and/or a tablet, principally made from an inorganic or organic powder, paper or non-woven fabric principally made from pulp, non-woven fabric and/or woven fabric principally composed of a plastic material, non-woven fabric and/or woven fabric principally composed of an animal or plant derived substance, a foam principally composed of a plastic material, a plastic incorporated body, dried plant, gel, jelly or silica gel.

The body having a chemical contained therein is preferably serviced as accommodated in a chemical containing or carrier body retaining receptacle that is provided with at least one vent hole.

A chemical containing or carrier body retaining receptacle is provided in accordance with the present invention, which is characterized in that it is provided with at least one vent hole, is of a size sufficient to accommodate a chemical containing body therein, and has its inner surface spaced from the surface of the chemical containing body by a distance of 1 to 10 mm.

The chemical containing or carrier body retaining receptacle so constructed in accordance with the present invention has been found to permit vapor of the chemical to pass smoothly between the inner surface of the receptacle and the surface of the chemical containing body and to diffuse through a vent hole into its outside.

A chemical heating, volatilizing apparatus is provided in accordance with the present invention, which is characterized in that the apparatus includes a heater element on or above which a chemical containing or carrier body retaining receptacle is loadable having at least one vent hole, the said heater element having its heat releasing surface inclined at an angle of 0 to 70 degrees with respect to a plane on which the apparatus is placed.

The chemical heating, volatilizing apparatus so constructed in accordance with the present invention provides an arrangement with an inclined heat releasing surface of the heater element whereby the chemical containing body is heated in whole and the apparatus can be made up in a compact design.

An indicator for a heat volatilizing chemical is provided in accordance with the present invention, the indicator displaying a time period of service of the chemical, utilizing color change brought about by an irreversible reaction due to heating, the indicator being characterized in that a stage of service of the chemical in lapse of time from a start to an end point thereof is represented by a change of a mark from visible to invisible and a change of another mark from invisible to visible according to color and shade change, the two changes being caused to occur simultaneously in the indicator.

According to this aspect of the present invention, the presence in the indicator of two marks, i.e., a first mark changing from visible to invisible and disappearing and a second mark changing from invisible to visible and appearing enables the user to clearly recognize, and hence permits clearly conveying to the user, the depletion of the effective ingredient of the chemical when its end point is reached.

An indicator for a heat volatilizing chemical as mentioned above may specifically be so configured that a first mark changing from visible to invisible is caused to appear in a color representing the chemical's endpoint and a second mark changing from invisible to visible is caused to appear in a color representing the chemical's start point in the indicator.

According to the preceding specific form of implementation of the present invention, the combined change in visibility and invisibility of the first and second marks enables the user to clearly recognize, and hence permits clearly conveying to the user, the depletion of the effective ingredient of the chemical when its end point is reached.

An indicator for a heat volatilizing chemical as mentioned above may specifically be so configured that the change in color go on gradually in the indicator as time of heating elapses.

According to the preceding specific form of implementation of the present invention, observing the first mark gradually disappearing and the second mark gradually appearing enables the user to clearly-recognize, and hence permits clearly conveying to the user, the state of use of the chemical, i.e., the remaining amount of the effective ingredient of the chemical at any time stage of service thereof.

An indicator for a heat volatilizing chemical as mentioned above in a further preferred form of implementation thereof is characterized in that it has a laminated film structure comprising a color and shade changing layer that retains a color and shade changing substance therein, a printed layer that is made of a transparent film as its base material of a thickness of 5 to 30 microns and is disposed at a front side of said color and shade changing layer, and a base layer that is made of an opaque film as its base material of a thickness of 50 microns or more, is high in masking power and is disposed at the rear side of said color and shade changing layer.

These and other features, objects and advantages of the present invention will become more readily apparent to those of ordinary skill in the art from the following detailed description of the preferred forms of embodiment thereof as illustrated in the various drawing Figures.

BEST MODE FOR CARRYING OUT THE INVENTION

Figure 1:
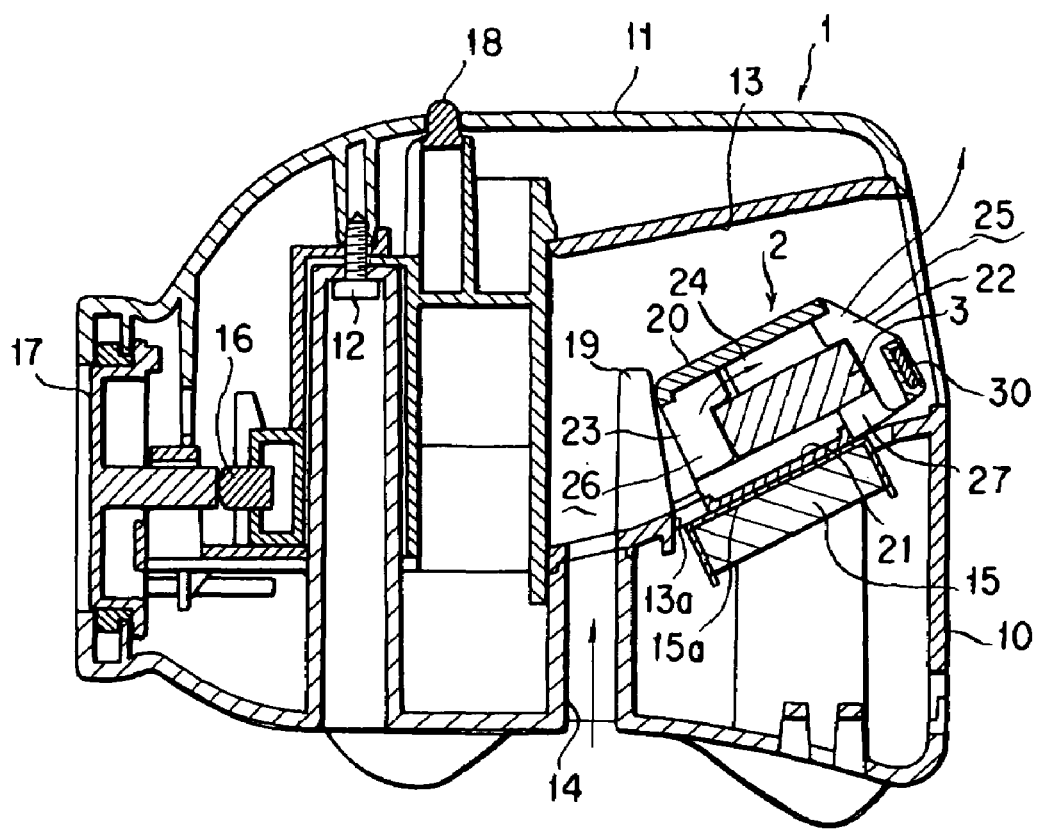
FIG. 1 is a vertical cross sectional view illustrating a chemical heating, volatilizing apparatus that represents a first form of embodiment of the present invention.

Referring now to FIG. 1, an explanation is given in respect of a chemical heating, volatilizing apparatus according to the first form of embodiment of the present invention.

The chemical heating, Volatilizing apparatus is made up of a chemical heating, volatilizing vessel 1, a chemical containing or carrier body retaining receptacle 2 and a chemical containing or carrier body 3 to be wholly heated or heated over its entirety. The chemical containing body retaining receptacle 2 integral with the chemical containing body 3 is denominated a chemical volatilizing body.

The chemical heating, volatilizing vessel 1 has a structure in which a lower and an upper casing 10 and 11 are coupled together with a machine screw or screws 12. The lower casing 10 is provided with a section 13 that is open rearwards and loaded with the chemical containing or carrier body 3. Also provided is an air intake section 14 opening to a lower forefront portion of the chemical containing body loading section 13. In an undersurface opening 13a of the chemical containing body loading section 13, a heater element 15 is attached to the lower casing 10, the heater element having a maximum surface temperature of 50 to 250° C.

The heater element 15 has a heat releasing surface 15a inclined to the horizontal and exposed to the chemical containing body loading section 13.

The lower casing 10 also has a switching part 16, a push button 17 and a lamp 18 attached thereto. The push button 17 may be pressed to turn on the switching part 16, which causes the heater element 15 to emit heat and the lamp to be lit up when they are electrically energized by a power supply.

The chemical containing body retaining receptacle 2 as shown also in FIGS. 2 to 7 exhibits a box-like configuration as having an upper plate 20, a lower plate 21, a front plate 22, a rear plate 23 and a pair of opposed side plates 24, and is formed with an air outlet 25 in the front plate 22 and an air inlet 26 in the rear plate 23.

A gap 27 is provided between the front plate 22 and the lower plate 21, the latter being made detachable.

Figure 5:
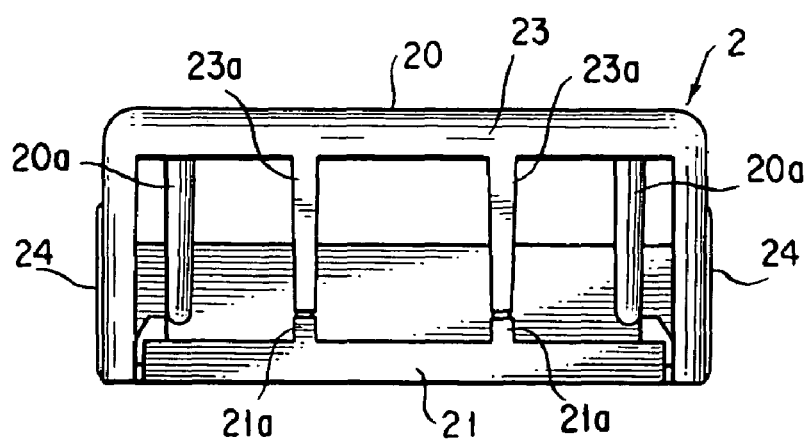
FIG. 5 is a rear side elevational view of this chemical containing body retaining receptacle.
Figure 6:
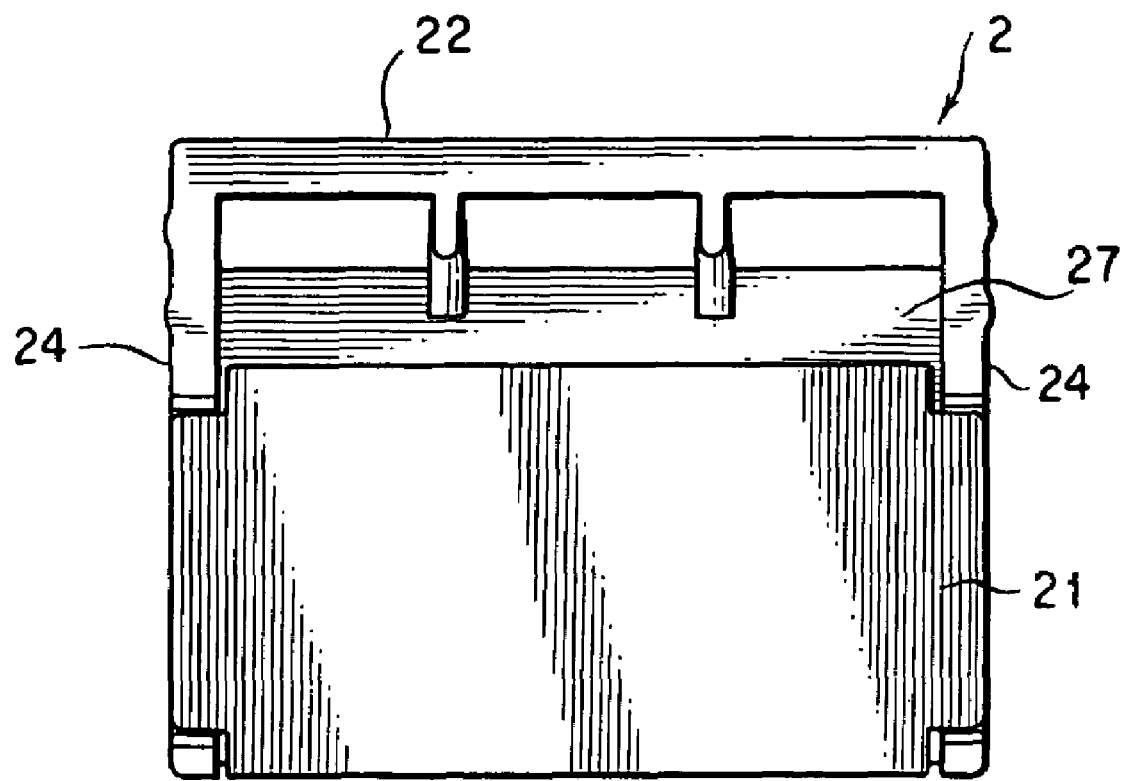
FIG. 6 is a bottom plan view of this chemical containing body retaining receptacle.
Figure 7:
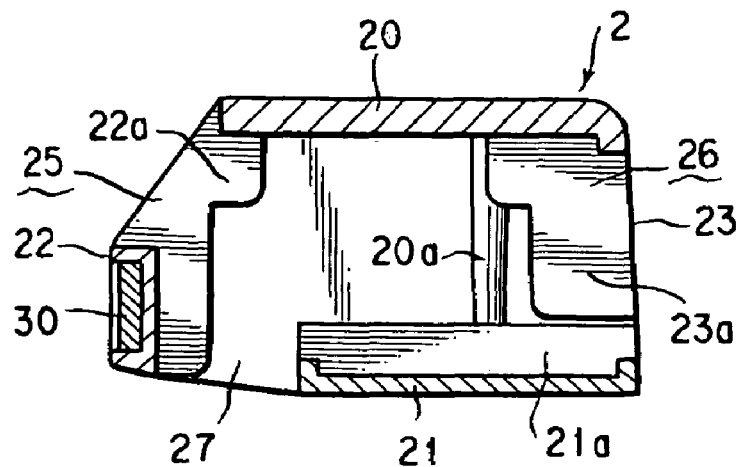
FIG. 7 is a cross sectional view taken along the line VII-VII in FIG. 3.

The inner surface of the lower plate 21 as can be seen from FIGS. 5 and 7 is formed integrally with a plurality of ridges or elongate raised portions 21a. each extending in a front and back direction of the retaining receptacle 2.

Figure 2:
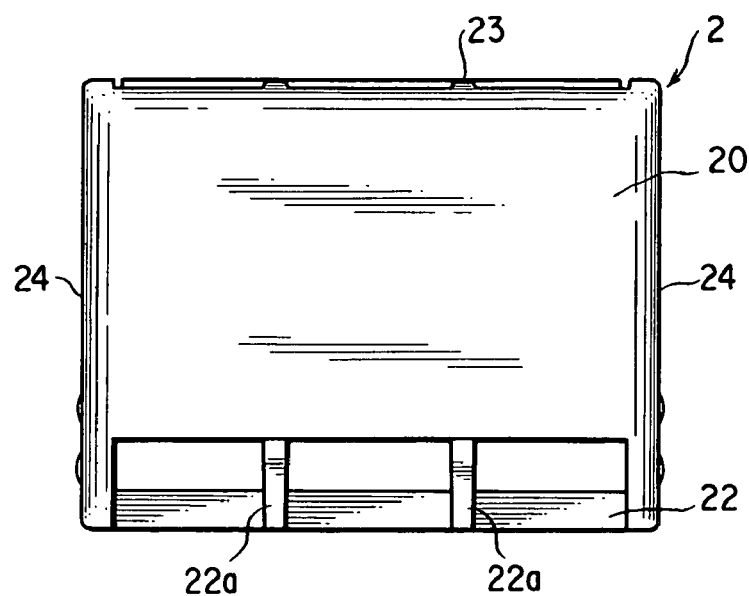
FIG. 2 is a top plan illustrating a chemical containing body retaining receptacle included in the apparatus shown in FIG. 1.
Figure 3:
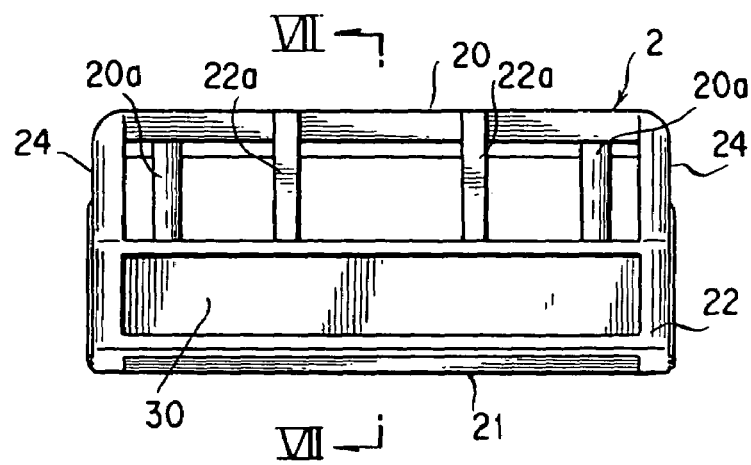
FIG. 3 is a front side elevational view of this chemical containing body retaining receptacle.
Figure 4:
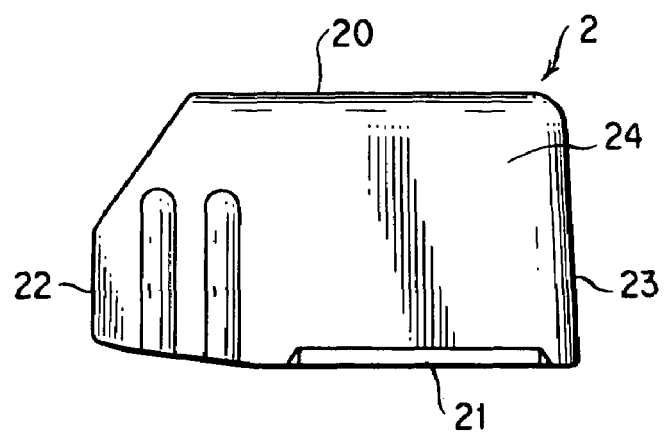
FIG. 4 is a right hand side elevational view of this chemical containing body retaining receptacle.

The front plate 22 as can be seen from FIGS. 2, 3 and 7 has in its inner surface a plurality of front vertical pieces 22a attached integrally thereto, and also has in its outer surface an indicator 30 mounted thereon.

The rear plate 23 as can be seen from FIGS. 5 and 7 is formed in its inner surface with a plurality of rear vertical pieces 23a integrally, which are made in contact with the ridges or raised portions 21a, respectively, at positions closer to the rear ends thereof.

Further, as shown in FIGS. 3, 5 and 7 the upper plate 20 is formed in its inner surface with rods 20a each in the form of a round bar, integrally and facing downwards.

This chemical containing body retaining receptacle 2 is inserted into and loaded in the chemical containing body loading section 13 in the chemical heating, volatilizing vessel 1 shown in FIG. 1 so that its lower plate 21 may lie in contact with the heat releasing surface 15a of the heater element 15 and the rear plate. 23 may be touched and thereby held against slipping down by a stopper 19 as shown in FIG. 1.

The chemical containing body 3 has a chemical contained therein that when heated is capable of escaping in vapor, and as a whole assumes a rectangular parallelepiped outline. The chemical containing body 3 can be loaded into and accommodated in the chemical containing body retaining receptacle 2 upon removing the lower plate 21 therefrom.

Figure 8:
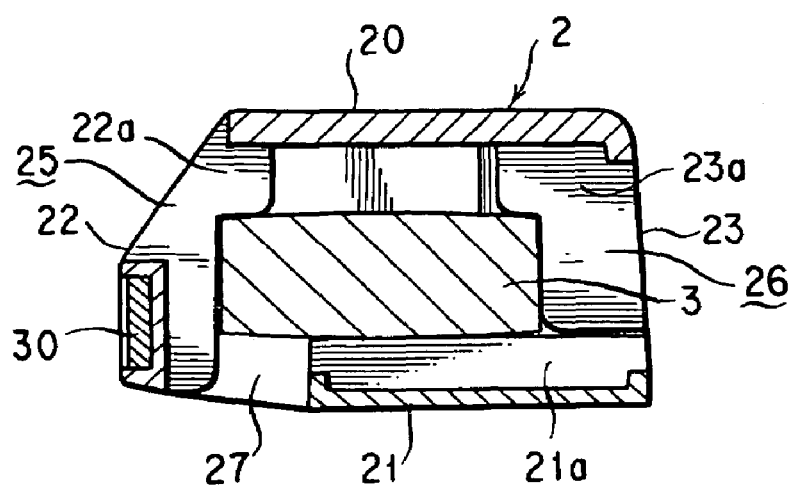
FIG. 8 is a cross sectional view illustrating such a chemical containing body retaining receptacle while in service in the chemical heating, volatilizing apparatus shown in FIG. 1.

As shown in FIG. 8, the chemical containing body so accommodated has its surface made in contact with the front vertical pieces 22a and the rear vertical pieces 23a and also with the rods 20a at the right and left hand sides, and provides between this surface and the inner surface or wall of the chemical containing body retaining receptacle 2 a gap through which vapor of the chemical passes.

Beneath the chemical containing body 3 there lie the ridges 21a in contact therewith. The rising height of these ridges 21a may be altered to change the distance between the heater element 15 and the chemical containing body 3, thereby adjusting the amount of evaporation of the chemical at a desired level.

The amount of evaporation of the chemical may also be adjusted, though not illustrated in the Figures, by providing the lower plate with a ridge or piece projecting downwards to change the distance between the heater element 15 and the chemical containing body 3.

Referring to FIG. 1, in the state that the chemical heating, volatilizing apparatus 1 is loaded therein with the chemical containing body retaining receptacle 2, actuating the heater 15 causes air to flow from the air intake section 14 and flow through the air inlet 26, the gap and the air outlet 25, then out of the apparatus as indicated by the arrows shown.

That is to say, the heater element 15 by emitting the heat produces a rising current of air as indicated by the arrows as shown, which permits vapor of the chemical to diffuse smoothly.

Next, a further detailed explanation is given in respect of the chemical containing body retaining receptacle 2.

The chemical containing body retaining receptacle 2 is structurally sufficient if it can accommodate the chemical containing body 3 in it and if it is provided with one or more vent holes. For the latter requirement, any structure is sufficient that permits air to flow and pass through its interior through one or more vent holes.

The chemical containing body retaining receptacle 2 may be composed of at least one resin selected from the group that consists of polyolefin, polyester, polyamide and polysulphone resins.

The surface of the chemical containing body 3 and the inner surface of the receptacle 2 are spaced apart from each other across the gap 27 at a distance of 1 to 10 mm, preferably 1 to 5 mm.

That is to say, as the gap reduced to zero makes vapor unable to pass it and the gap made too large makes it unable to hold its required heat retaining property, the distance is ranged to be between 1 and 10 mm, preferably 1 to 5 mm, as mentioned above to meet the least requirements that vapor of chemical pass without hindrance and yet that its heat retaining property be adequately held.

Mention is next made of results of tests in which the amount of evaporation by a specified amount of the chemical is measured by varying the distance between the surface of the chemical containing body 3 and the inner surface of its retaining receptacle 2 under the conditions stated below.

[Condition]

For the chemical containing body 3, use is made of a tablet, which is formulated with 3000 mg of a chemical that consists of prallethrin as an active ingredient.

The amount of the active ingredient as the chemical is quantitatively determined by a gas chromatograph using acetone to extract the ingredient trapped in silica gel.

The appraisal is taken to judge the amount of evaporation by the specified amount of the active efficacious ingredient in excess of 90% as acceptable (marked O against unacceptable marked X).

The test results are shown in Table 1 below.

TABLE 1

| Distance between Chemical containing body and Receptacle Inner surface (mm) | Amount of Evaporation by Specified Amount of the Chemical (%) | Appraisal |
| --- | --- | --- |
| 15 | 78.4 | X |
| 10 | 99.4 | O |
| 5 | 96.4 | O |
| 1 | 94.7 | O |
| 0.5 | 70.3 | X |

From these test results, it has been turned out that an appropriate distance between the surface of the chemical containing body 3 and the inner surface of its retaining receptacle 2 lies in the range between 1 and 10 mm.

The chemical heating, volatilizing apparatus according to the present invention can be laid out in a compact design by reason of the fact that the heater element 15 is laid in inclination with the horizontal as mentioned above.

This in turn is because of the fact that while the presence of an obstacle above the rising current of air carrying the chemical volatilized by heating brings about disadvantages such as a loss of the chemical and a contamination of the apparatus, the heater element if placed horizontally requires the apparatus to include an arch such as to pass the current of air smoothly without causing these disadvantages and thus requires the apparatus to be made larger in size.

Therefore, the heater element 15 is made inclined advantageously at an angle ranging up to a maximum angle of inclination of 70 degrees. If, however, the size of the apparatus does not pose any problem, the heater may be placed horizontally. Accordingly, the angle at which the heater element may be mounted to the apparatus can range between 0 and 70 degrees with respect to the plane on which the apparatus is installed.

The apparatus in service has its contour or outside temperature rising to not more than 60° C.

An explanation is next given in respect of the whole heated, chemical containing body 3.

Figure 9:
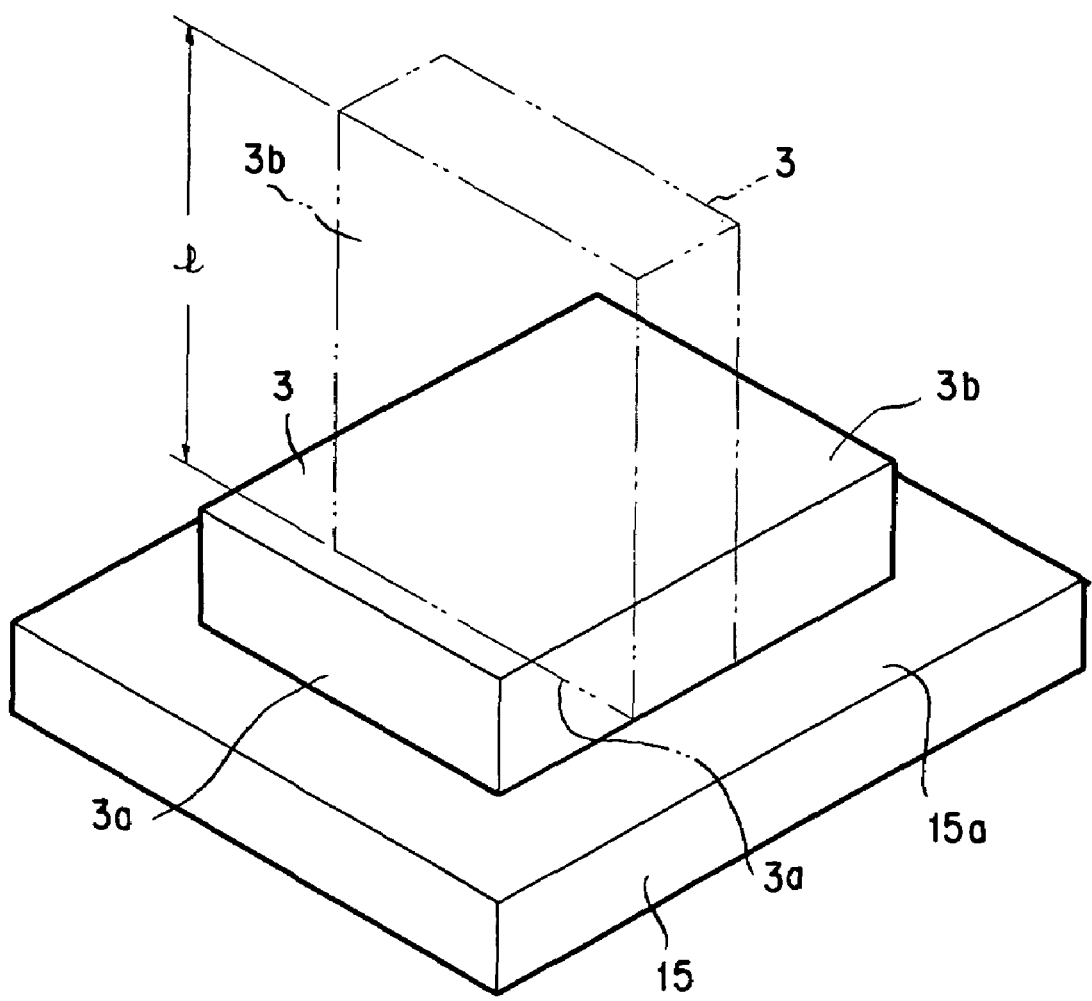
FIG. 9 is a perspective view illustrating a chemical containing body for use with its retaining receptacle shown in FIGS. 1 to 8.

The chemical containing body 3 as shown in FIG. 9 is in the form of a rectangular parallelepiped plate, and has a planar size smaller than that of the heat releasing surface 15 of the heater element 15.

This makes it possible to heat the chemical containing body 3 over its entirety directly or indirectly by means of the heater element.

The body 3 for containing the chemical is made of a material that can contain and hold the chemical and that may comprise, e.g., at least one material selected from the group that consists of a caked body and/or a sintered body and/or a tablet, principally made from an inorganic or-organic powder, paper or non-woven fabric principally made from pulp, non-woven fabric and/or woven fabric principally composed of a plastic material, non-woven fabric and/or woven fabric principally composed of an animal or plant derived substance, a foam principally composed of a plastic material, a plastic incorporated body, dried plant, gel, jelly or silica gel.

A caked body and/or a sintered body and/or a tablet principally made from an inorganic or organic powder as mentioned above may be a solid body as described in JP 6-192008 A, which can in addition to calcium phosphate as its principal component contain an excipient (crystalline cellulose) and a binder (CMC) as required for caking, a binder (plastic powder or nylon powder) as required for sintering and a glossing agent (magnesium stearate) as required for tableting.

The abovementioned paper and/or non-woven fabric, principally made from pulp, while meaning in general what is commonly referred to as paper, may possibly contain a plastic material. The paper body for chemical containment can be made using water or alternatively using thermal or adhesive joining.

The abovementioned non-woven fabric and/or woven fabric principally composed of a plastic material correspond to a non-woven and/or a woven fabric as they are commonly called. The methods of making the non-woven fabric body for chemical containment can be largely classified into dry-type methods using heat or adhesive and wet-type methods in which fibers are entwined with water or an organic solvent.

Among the others, the abovementioned non-woven fabric and/or woven fabric principally composed of an animal or plant derived substance refer to what are commonly called a non-woven and a woven fabric made of silk, cotton, flax, kenaf, gelatin or the like.

The abovementioned foam principally composed of a plastic material basically signifies a polyurethane, polyethylene, polypropylene or polystyrene foam mainly used now as a cushion or sponge material, but in a broader sense is intended to mean a porous plastic body. After all, a porous plastic body that can be impregnated with a chemical is signified.

The plastic incorporated body means a molded mixture of a plastic material with a chemical and a plasticizer blended at need for its volatilization from and its migration inside of the body.

The dried plant indicates a dried flower or fruit and can be exemplified by a potpourri, a luffa or wood.

The gel designates not only a material, such as gelatin, carrageenan and gellan gum, solidified using a gelling agent, but also a material solidified using a polymeric water or oil absorbing agent.

The jelly refers to a pasty material obtained by mixing an organic and/or an inorganic powder with a chemical and a solvent and bodying up the mixture. This material when the chemical and solvent are volatilized has its body disintegrated, returning to powder and it thus makes clear its end point (the point of time at which its chemical efficacy terminates).

The chemical that is contained by the chemical containing body 3 may be an insecticide, in particular a pyrethroid insecticide, a microbicide, a repellent, a growth control chemical, an aromatic or a deodorant, which has a vapor pressure of not less than $1.0 \times 10^{-5}$ mmHg as a measure.

The substance that can be compounded with the chemical to form the chemical containing body 3 includes a heat stabilizer, an oxidation inhibitor, an ultraviolet absorbing agent, a dye, a pigment, an aromatic/deodorant and an efficacy synergistic agent.

An explanation is next given in respect of how the chemical containing body 3 when heated can be rendered able to keep the chemical volatilizing for an extended period of time, namely longer than 12 hours.

1. The chemical containing body 3 has a thickness of not less than 3 mm.
2. The percentage loss of heat L expressed by the formula: $L=[(h-t)/h] \times 100$ is not greater than 70%, where h and t are the heating temperature for and the lowest temperature of the chemical containing body 3, respectively.

Volatilization by heating here means heating the chemical containing or carrier body 3 to an extent such that it has its temperature raised to at least 5 higher than the room temperature, a temperature enough for the chemical to be emitted into air.

The thickness of the chemical containing body means a distance measured from its surface that is the closest to the heater element, i.e., its bottom surface to its surface that is the farthest from the heater element, i.e., its top surface. It does not mean the thickness of a portion of the chemical containing body that is the thinnest. For example, as shown in FIG. 9, in case the chemical containing body 3 is used as placed with a surface thereof 3a smaller in thickness or smaller in area lying on or above the heater element 15 as indicated by the imaginary line, the thickness is represented by the length 1 of a longer side of the surface thereof that is wider in area. What is, important here is a specific material with its specific physical properties of the chemical containing body, inter alia a high thermal efficiency that gives a minimum dissipation of heat to the chemical containing body if placed apart from the heater element.

The percentage loss of heat mentioned above is the synonym of thermal conductivity. While the temperature setting for the heater element used may be made in accordance with the chemical to be volatilized, efficient utilization of energy without waste requires the loss of heat here to be limited to 70% or less.

The heating temperature h used here as a basis for computing the percentage loss of heat is indicated by the maximum surface temperature measured of the heater element.

Mention is next made of tests in which measurement is made to determine the volatilization lasting time period of how long the chemical containing body continues to volatilize the chemical for various amounts of its thickness and the percentage loss of heat that are varied under the following conditions.

[Conditions]

Use is made of a heating, volatilizing apparatus of mat type.

The chemical containing body is placed directly on the heater element.

A thermocouple thermometer is used for temperature measurement.

Measurement is taken under isothermal conditions.

Appraisal is taken to judge as acceptable (marked O against unacceptable marked X) the test results in which the amount of volatilization by the specified amount of the chemical is more than 90% and the volatilization lasting time period is longer than 12 hours.

For the chemical containing body, use is made of a pulp mat having terallethrin compounded or distributed therein.

The amount of the active ingredient as the chemical is quantitatively determined using acetone to extract the ingredient trapped in silica gel.

The test results are shown in Table 2 below.

TABLE 2

| Test No. | Chemical containing body | Size Width × Length × Height (Thickness) (mm) | Heater Element Temp. (° C.) | Body Top Surface Temp. (° C.) | Heat Loss (%) | Amount of Impregnation of Chemical expressed in Chemical Lasting Time (Hrs.) | Amount of Volatilization by Specified Amount of Chemical (%) | Appraisal |
|---|---|---|---|---|---|---|---|---|
| 1 | Pulp Mat | 35 × 21.5 × 2.3 | 170.7 | 114.1 | 33.2 | 12 | 99.1 | X |
| 2 | Pulp Mat | 35 × 21.5 × 4.6 | 169.4 | 93.5 | 44.8 | 24 | 98.7 | O |
| 3 | Pulp Mat | 35 × 21.5 × 6.9 | 169.3 | 79.7 | 52.9 | 36 | 97.2 | O |
| 4 | Pulp Mat | 35 × 21.5 × 9.2 | 169.3 | 66.7 | 60.6 | 48 | 94.2 | O |
| 5 | Pulp Mat | 35 × 21.5 × 11.5 | 169.4 | 53.5 | 68.4 | 60 | 90.6 | O |
| 6 | Pulp Mat | 35 × 21.5 × 13.8 | 170.7 | 42.5 | 75.1 | 72 | 82.3 | X |

From these test results, it is seen that any thickness less than 3 mm gives rise to enough amount of chemical volatilization but reduces the chemical volatilization lasting time period to 12 hours or less. On the other hand, even increasing the thickness to 13.8 mm (i.e., not less than 3 mm) does not yield enough amount of chemical volatilization if the percentage loss of heat is 75.1% (i.e., more than 70%).

From these findings, it has been confirmed that making the thickness of the chemical containing-body not less than 3 mm and the percentage loss of heat not more than 70% permit the chemical to remain volatilized stably for a long period of time, longer than 12 hours.

An explanation is next given in respect of the indicator 30 shown attached to the front plate 22 of the chemical containing body retaining receptacle 2.

This indicator 30 is made visible from the chemical containing body loading section 13.

The indicator 30 is designed to indicate and display the time period of service of the chemical, utilizing color and shade changes brought about by irreversible reaction caused due to heating. The state of service of the chemical with the lapse of time from the chemical start point towards its end point is represented by visibility changes of colors produced simultaneously at two or more sites, i.e., a change of one mark from visible to invisible and a change of another mark from invisible to visible that take place concurrently.

More specifically, this is an indicator that is provided with a color and shade changing section that exhibits a change in color and shade from a start color to an end color produced utilizing a color and shade change caused by an irreversible reaction due to heating, a first mark that represents the chemical start point with the end color and a second mark that represents the chemical end point with the start color.

The color and shade changing section is designed to commence heating when the heating of the chemical for volatilization is started and to gradually change its color and shade from the start color towards the end color with the lapse of time of the heating. And, the completion of color change to the end color and the depletion of the active ingredient of the chemical, i.e., the chemical end point are made to coincide.

This makes the state of service of the chemical, viz., the remaining amount of the active ingredient of the chemical well noticeable by the user.

The extent of the color changes if indicated by its color difference $\Delta E$, it becomes not less than $\Delta E=10$.

Therefore, it has good visibility to look at.

To the contrary, visibility to look at is clearly diminished if $\Delta E$ is less than 10.

The highest temperature at which the color and shade changing section changes the color and shade may range between 35 and 200° C.

Figure 10:
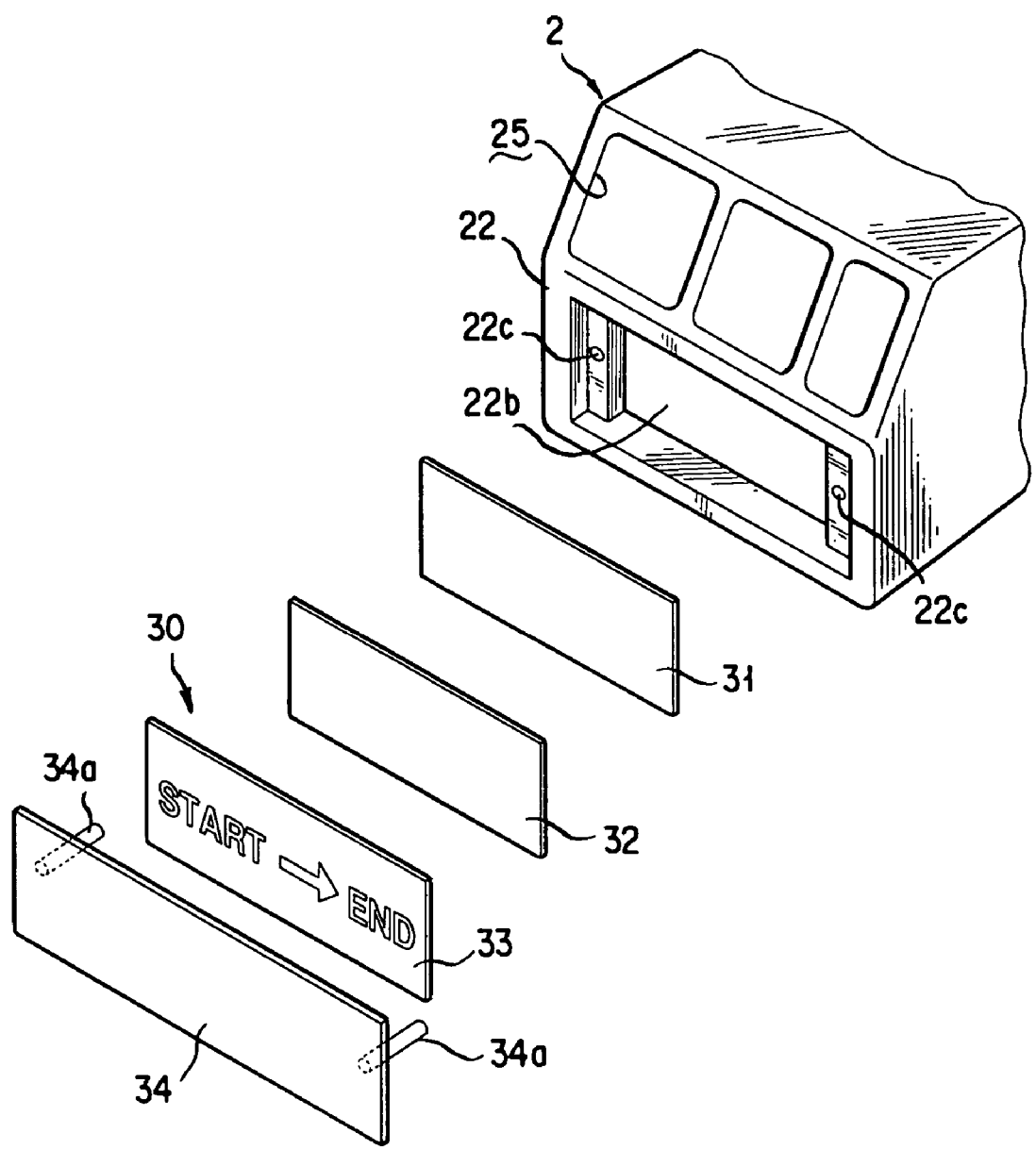
FIG. 10 is a decomposed perspective view illustrating an indicator in its first form of embodiment according to the invention, together with a means for attaching it to such a chemical containing body retaining receptacle as shown in FIGS. 1 to 8.

Referring to FIG. 10, mention is first made of the indicator 30 as regards a concrete configuration thereof.

The indicator 30 has a laminated film structure having a base layer 31, a color and shade changing layer 32 and a printed layer 33 laid one to the next, and is provided with a plate 34 with which the surface of the printed layer 33 is covered.

While in FIG. 10 the base layer 31 and the print layer 33 are shown separated apart from the color and shade changing layer 32, they has in fact been fast attached in advance to the color and shade changing layer 32 so as to place it between them.

The contact laminate of the base layer 31, the color change layer 32 and the print layer 33 is mounted to the chemical containing body retaining receptacle 2 by fitting the same into a recess 22b formed in the front plate 22 thereof.

The covering plate 34 has a pair of pins 34a and is secured to the front plate 22 with these pins 34a fitted into holes 22c formed in the plate 22.

The base layer 31 is made up of as an opaque film material of 50 microns or more in thickness, which is high in masking power. The basic layer 31 has a role assigned when the indicator 30 is installed to provide a masking function of rendering the color visibility of the indicator 30 the least affected by the color of the chemical containing body retaining receptacle and others. The other role assigned to the basic layer 31 is to adjust the basic physical properties of the indicator's components as they relate to its manufacturing steps such as blanking, stamping and/or punching, cutting, aligning, sucking, extruding, etc.

The color and shade changing layer 32 carries and holds a thermally color and shade changing substance, and constitutes the color and shade changing section mentioned above.

The color and shade changing layer 32 prior to color and shade changing has a color (start color) identical to that of the base layer 31.

The thermally color and shade changing layer 32 is made up of three sub-layers, first, second and third. The first sub-layer is constituted by a support impregnated or coated with one of two chemicals that when mixed together or contacted with each other exhibit a color or discolor reaction, or constituted alternatively by film obtained when one of such two chemicals is dissolved in or decomposed with a film forming component. The second sub-layer is constituted by a resin film disposed on the first layer to cause diffusion-migration of at least one of the two chemicals. The third layer is a layer disposed on the second layer and containing the other of the two chemicals. The color or discolor reaction is a reaction that takes place when an acid-base substance and an acid-base indicator, an oxidizing-reducing agent and an oxidation-reduction indicator, or a metallic compound and a chelating agent are mixed together or contacted with each other. For the resin film as the second layer parting the first and third layer and causing diffusion and migration when heated, use is made of a thermally coloring polyester, polyamide and/or acrylic lamination.

The printed layer 33 is made of a transparent film of 5 to 30 microns in thickness.

This transparent film has display marks or characters printed typically on its rear surface, i.e., on its surface adjacent to the color and shade changing layer 32.

The abovementioned transparent film has the function to protect the color and shade changing layer 32 and also has a moderate oxygen permeability.

The covering plate 34 is constituted with a transparent film and has an ultraviolet absorbing agent admixed therein.

This plate 34 prevents an ultraviolet light from impinging on the color and shade changing layer and keeps it from discoloring thereby.

Also, the printed layer 33 may have an ultraviolet absorbing agent incorporated therein or applied thereon.

Mention is next made of a first embodiment of the indicator 30 according to the present invention.

Here, the base layer 31 is white, while the color and shade changing layer 32 is white before its color and shade changing and is red after its color has been changed.

The printed layer 33 as shown in FIG. 10 has characters "START", a first mark representing the chemical's start point printed in red, characters "END", a second mark representing the chemical's end point printed in white, and an arrow headed from the "START" characters' side towards the "END" characters' side printed, thereon.

That arrow is graduation printed so that its "START" characters' side is printed in red, becoming thinner towards its "END" characters' side that is printed in white.

Figure 11:
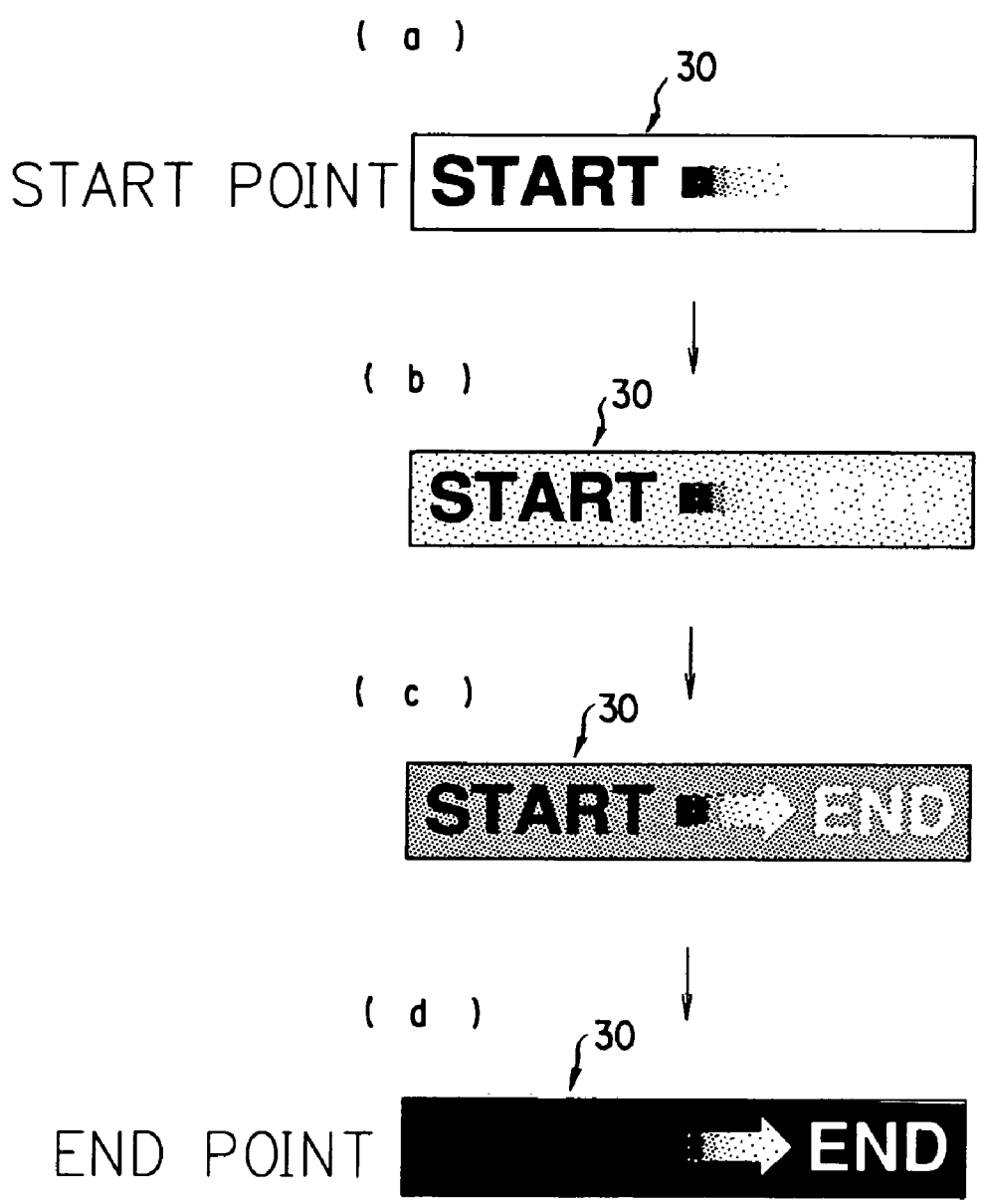
FIG. 11 is a diagrammatic view illustrating changes in color and shade in the indicator shown in FIG. 10.

The indicator 30 when the heating, volatilization of the chemical is started presents the appearance as shown in FIG. 11, at the stage (a) that the "START" characters and only a root portion of the arrow closer to those characters visibly appear.

With a lapse of the chemical's heating time, the color and shade changing layer 32 changes its color to red lighter in shade, and the indicator 30 assumes the appearance that the "END" characters are dimly visible as shown in FIG. 11, at the stage (b). At this stage, difference in shade of red between the "END" characters and the color and shade changing layer 32 is small or minimal.

With a further lapse of the chemical's heating time, the color and shade changing layer 32 changes its color to red somewhat darker in shade, and the indicator 30 comes to take the appearance that the "END" characters are somewhat more clearly visible as shown in FIG. 11, at the stage (c).

Thus, the indicator 30 by changing its appearance as the chemical's heating time elapses makes it possible for the user to recognize the chemical's heating time, that is the residual amount of the chemical left contained in the chemical containing body 3 by observing the degree difference in shade of red between the "START" characters and the color and shade changing layer 32.

At the end point of the chemical when the chemical's heating time ends, i.e., when the residual amount of the chemical left contained in the chemical containing body 3 becomes less that an effective level, the "START" characters on the printed layer 33 and the color and shade changing layer 32 become identical to each other in shade of red, thereby making those characters invisible. Now, the indicator thus presents the appearance that the "START" characters are hidden from sight and the "END" characters alone are clearly visible as shown in FIG. 11, at the stage (d).

This having been the case enables the user then to clearly recognize that the active ingredient of the chemical proves to be inefficacious.

Mention is next made of a second embodiment of the indicator 30.

Here again, the base layer 31 is white, while the color and shade changing layer 32 is white before its color and shade changing and is red after its color has been changed.

Figure 12:
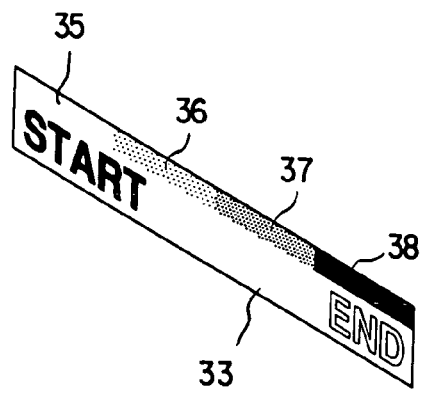
FIG. 12 is a perspective view illustrating a printed layer for an indicator in its second form of embodiment according to the invention.

As shown in FIG. 12 the printed layer 33 in addition to having the characters "START" printed in red and the characters "END" printed in white has here, a first band region 35 printed in white, a second band region 36 printed in red lighter in shade, a third band region 37 printed in red somewhat darker in shade, and a fourth band region 38 printed in red identical in shade to the "START" characters, thereon in succession between its opposite ends.

Figure 13:
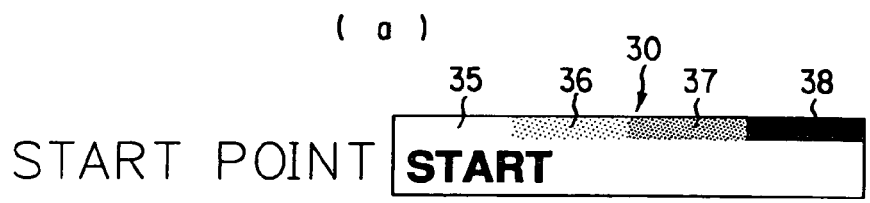
FIG. 13 is a diagrammatic view illustrating changes in color and shade in the indicator shown in FIG. 12.
Figure 13:
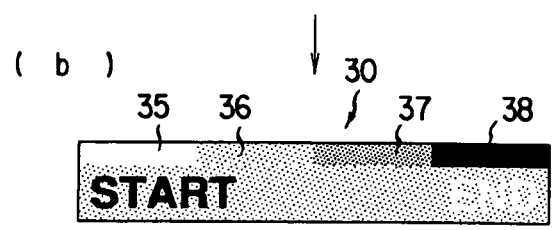
Figure 13:
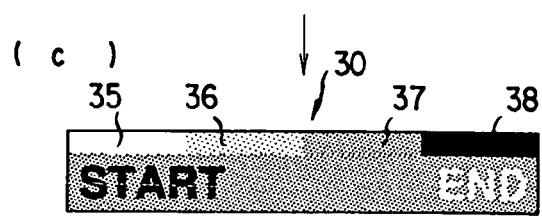
Figure 13:
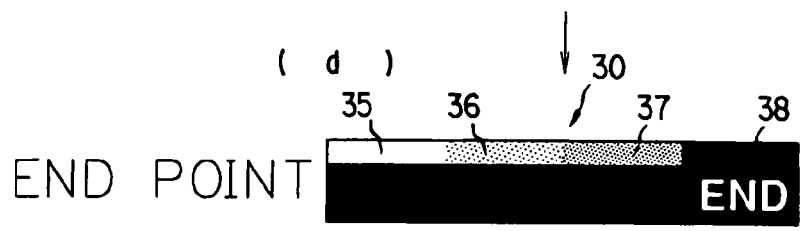

The indicator 30 when the heating volatilization is initiated presents the appearance as shown in FIG. 13, at the stage (a) that the "START" characters and the second, third and fourth band regions 36, 37 and 38 are visible.

With a lapse of the chemical's heating time, the color and shade changing layer 32 changes its color to red lighter in shade, and the indicator 30 assumes the appearance that the first band region 35 becomes visible, the third and fourth band regions 37 and 38 remain visible and the second band region 36 becomes invisible as shown in FIG. 13, at the stage (b).

With a further lapse of time, the color and shade changing layer 32 changes its color to red somewhat darker in shade, and the indicator 30 comes to assume the appearance that the first and fourth band regions 35 and 38 remain visible, the second band region 36 becomes again visible and the third band region 37 becomes invisible as shown in FIG. 13, at the stage (c).

At the end point of the chemical when the chemical's heating time ends, the indicator 30 presents the appearance as shown in FIG. 13, at the stage (d) that the "END" characters and the first, second and third band regions 35, 36 and 37 are visible while the fourth band region 38 becomes invisible.

In this way, the user is enabled to recognize progressive lapses of the chemical's heating time from changes in visibility of the first, second, third and fourth band regions 35, 36, 37 and 38 as well.

Further, the changes in visibility of the "START" characters and the "END" characters take place here as the same manner as in the first embodiment.

Figure 14:
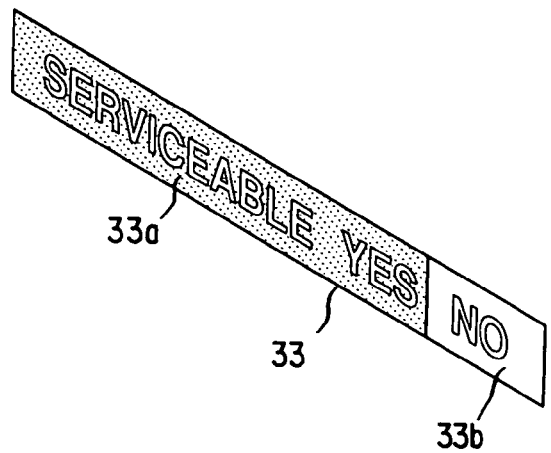
FIG. 14 is a perspective view illustrating a printed layer for an indicator in its third form of embodiment according to the invention.
Figure 15:
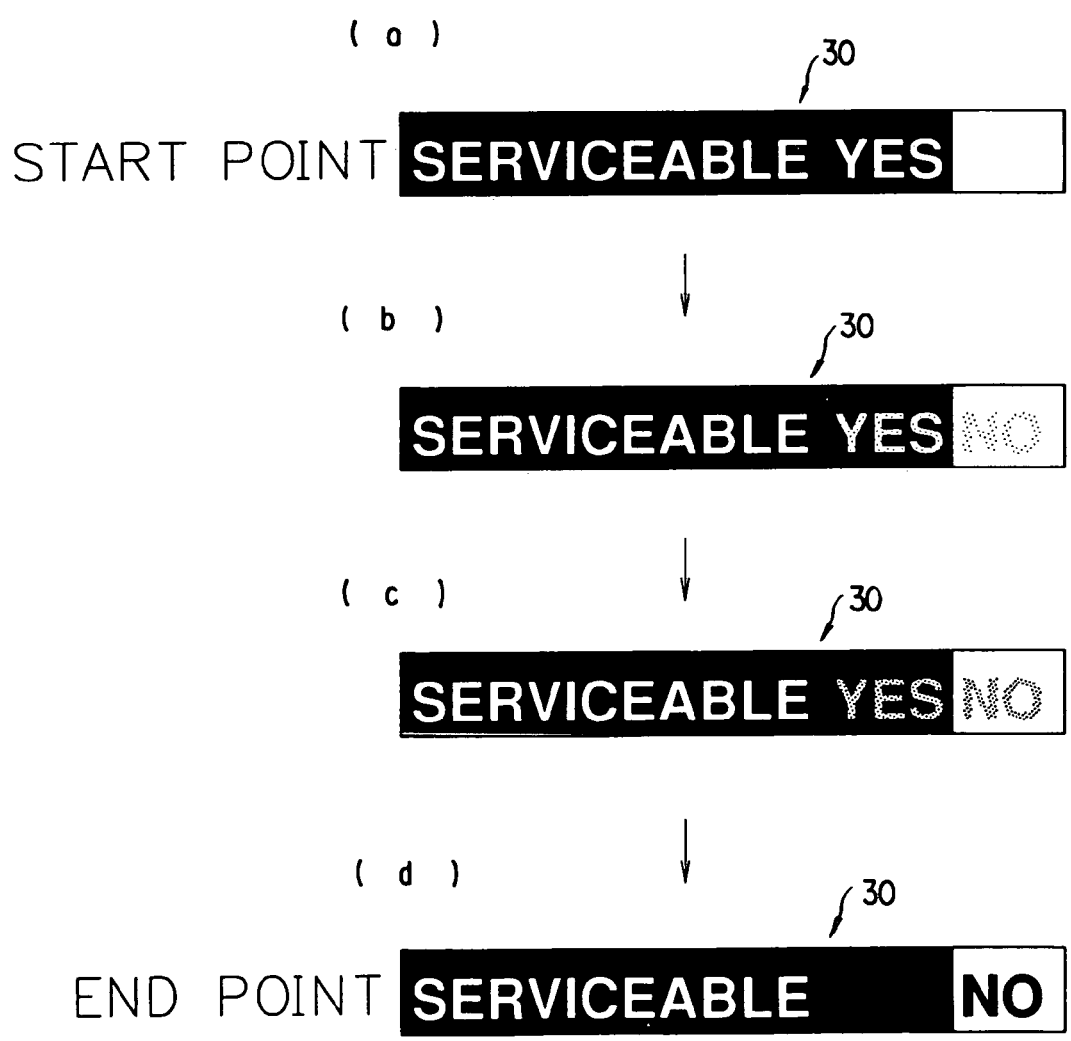
FIG. 15 is a diagrammatic view illustrating changes in color and shade in the indicator shown in FIG. 14.

Mention is next made of a third embodiment of the indicator 30 with reference to FIGS. 14 and 15.

As shown in FIG. 14, the printed layer 33 made of a transparent film has a left hand side half 33a printed in red except for characters "Yes" and its remaining right hand side half 33b printed in white except for characters "No".

The printed layer 33 further has characters "Serviceable" printed in white to the left of the characters "Yes" transparently taken out in the left hand side half 33a.

When the chemical's heating volatilization is initiated, the indicator 30 here presents the appearance as shown in FIG. 15, at the stage (a) that the characters "Serviceable Yes" are visible.

With the lapse of the chemical's heating time, the color and shade changing layer 32 is gradually changing its color and shade to red, and the indicator 30 is changing its appearance such that the characters "Yes" are becoming gradually darker in shade and invisible from visible while the characters "No" are becoming gradually clearer in shade and visible from invisible as shown in FIG. 15, at the stages (b) and (c).

At the end point of the chemical when the chemical's heating time period ends, the indicator takes the appearance that the characters "Yes" become utterly invisible while the characters "No" become clearly visible, thus enabling the user to visually recognize the message characters "Serviceable No".

The indicator 30 preferably is mounted on the chemical heating, volatilizing apparatus 1 in the neighborhood of the heater element 15 where it is visible from its outside.

Figure 16:
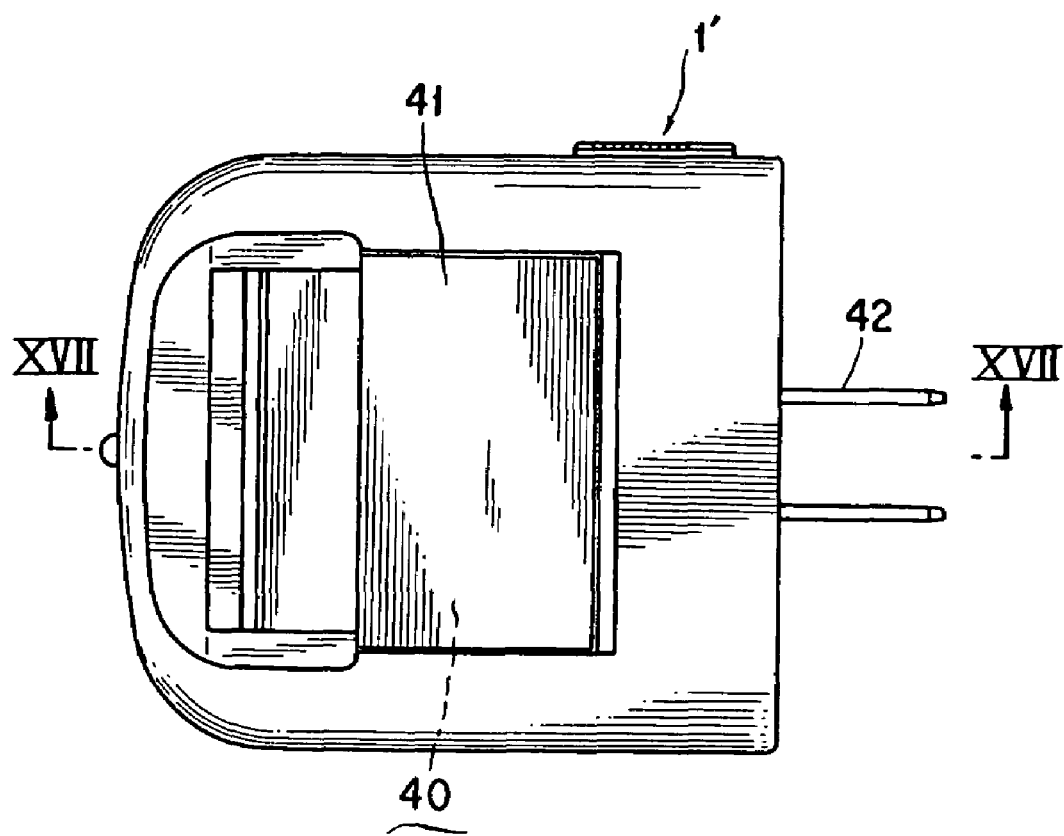
FIG. 16 is a top plan view illustrating a chemical heating, volatilizing apparatus that represents a second form of embodiment of the present invention.
Figure 17:
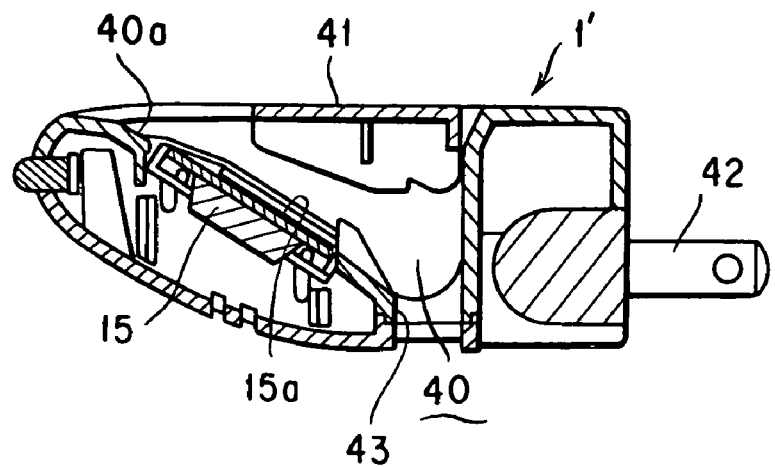
FIG. 17 is a cross sectional view taken along the line XVII-XVII in FIG. 16.
Figure 18:
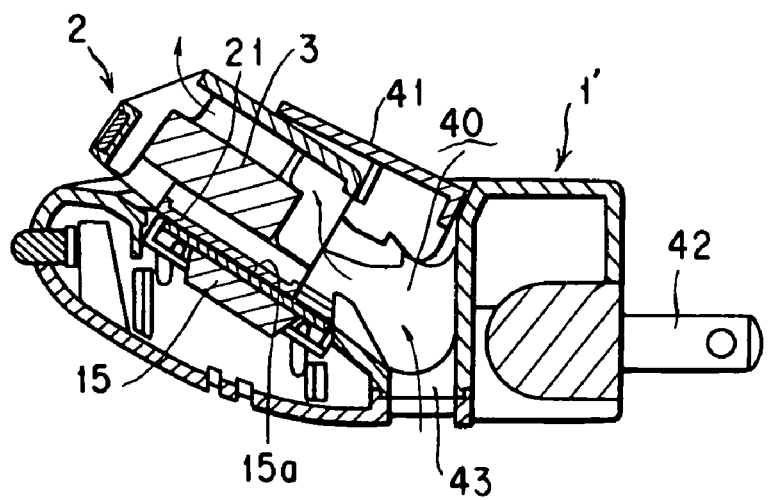
FIG. 18 is a cross sectional view of the chemical heating, volatilizing apparatus shown in FIGS. 16 and 17 and having a chemical containing body retaining receptacle set therein.

An explanation is next given in respect of a second form of embodiment of the chemical's heating, volatilizing apparatus with reference to FIGS. 16 to 18.

The chemical heating, volatilizing apparatus in this form of embodiment, indicated at 1', includes a recess section 40 open to top its surface, a lid 41 vertically turnable to open and close the recess section 40 and an attachment plug 42 for power supply.

The recess section 40 has its base surface 40a inclined to the horizontal, over which the heat releasing surface 15a of the heater element 15 projects.

The recess section 40 is open to the under surface through a vent section 43.

As shown in FIG. 18, with the lid 41 turned up, the recess section 40 is loaded with the chemical containing body retaining receptacle 2 so that the lower face plate 21 of the receptacle 2 lies in contact with the heat releasing surface 15a of the heater element 15.

Causing the heater element 15 to produce heat creates an air flow as indicated by the arrow through the apparatus, by which volatilization of the chemical is smoothly effected.

From the foregoing description, it is seen that a whole heated chemical containing or carrier body according to the present invention makes it possible to volatilize the chemical stably for an extended period of time.

It is also seen that a chemical containing or carrier body retaining receptacle according to the present invention causes vapor of the chemical to smoothly pass between an inner surface of the receptacle and the chemical containing body and to diffuse through a vent hole into its outside.

It is also seen that a chemical heating, volatilizing apparatus according to the present invention provides an arrangement with an inclined heat releasing surface of the heater element whereby the chemical containing body is heated in whole and the apparatus can be made up in a compact design.

It is further seen that an indicator for the heat volatilizing chemical conveys depletion of the chemical's active ingredient clearly and precisely to the user.

Although the present invention has been described hereinbefore in terms of the presently preferred forms of embodiments with respect to or implemented in a chemical containing body, a chemical containing body retaining receptacle, a chemical heating, volatilizing apparatus and an indicator for heat volatilizing chemical, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as compassing all alterations, modifications, or alternative applications as fall within the true spirit and scope of the invention.

What is claimed is:

1. A chemical heating, volatilizing apparatus comprising:
a heater element;
a chemical containing body, which contains a heat volatilizing chemical;
a chemical containing body retaining receptacle, which is loadable in the apparatus to be on or above the heater element, and which comprises at least one vent hole and which accommodates and retains the chemical containing body therein such that the chemical containing body is supported on a lower inner portion of the chemical containing body retaining receptacle and such that an upper inner surface of the chemical containing body retaining receptacle is spaced apart from an upper surface of the chemical containing body by a distance of 1 to 10 mm;
an indicator which indicates a stage of service of the heat volatilizing chemical from a start point to an end point of the service, and which comprises a first mark which changes from visible to invisible and a second mark that changes from invisible to visible simultaneously with the change of the first mark, due to color changes brought about by an irreversible reaction due to heating, so as to indicate the stage of service.

2. The chemical heating, volatilizing apparatus according to claim 1, wherein the upper inner surface of the chemical containing body retaining receptacle is spaced apart from the upper surface of the chemical containing body by a distance of 1 to 5 mm.

3. The chemical heating, volatilizing apparatus according to claim 1, wherein the chemical containing body is made of at least one material selected from the group consisting of: a caked body principally made from one of an inorganic powder and an organic powder; a sintered body principally made from one of an inorganic powder and an organic powder; a tablet principally made from one of an inorganic powder and an organic powder; a paper principally made from pulp; a non-woven fabric principally made from pulp; a non-woven fabric principally composed of a plastic material; a woven fabric principally composed of a plastic material; a non-woven fabric principally composed of an animal or plant derived substance; a woven fabric principally composed of an animal or plant derived substance; a foam principally composed of a plastic material; a plastic incorporated body; a dried plant; a gel; a jelly; and silica gel.

4. The chemical heating, volatilizing apparatus according to claim 1, wherein the lower inner portion of the chemical containing body retaining receptacle comprises a plurality of ridges which project from a lower surface of the chemical containing body retaining receptacle and which support the chemical containing body.

5. The chemical heating, volatilizing apparatus according to claim 1, wherein the at least one vent hole of the chemical containing body retaining receptacle include an air inlet hole and an air outlet hole.

6. The chemical heating, volatilizing apparatus according to claim 1, wherein the chemical containing body retaining receptacle comprises a front plate, a rear plate, an upper plate, a lower plate and a pair of side plates, wherein the lower inner portion of the chemical containing body retaining receptacle is provided at an inner side of the lower plate, and wherein the upper inner surface of the chemical containing body retaining receptacle is provided at an inner side of the upper plate.

7. The chemical heating, volatilizing apparatus according to claim 6, wherein the chemical containing body retaining receptacle further comprises:
a plurality of front projections which project inward from an inner surface of the front plate and which contact a front surface of the chemical containing body;
a plurality of rear projections which project inward from an inner surface of the rear plate and which contact a rear surface of the chemical containing body; and
a plurality of rods which project downward from the inner surface of the upper plate and each of which contacts one of a right surface and a left surface of the chemical containing body; and
wherein the lower inner portion of the chemical containing body retaining receptacle comprises a plurality of ridges which project from a lower surface of the chemical containing body retaining receptacle and which support the chemical containing body at a lower surface of the chemical containing body.

8. The chemical heating, volatilizing apparatus, according to claim 1, wherein the heater element has a heat releasing surface that is inclined by an angle $\Theta$ with respect to a plane defined by points on a bottom of the apparatus which support the apparatus when the apparatus is installed in a position for operation of the apparatus, and wherein $\Theta$ satisfies $0 < \Theta \leq 70$ degrees;
wherein the chemical containing body retaining receptacle is adapted to be loaded on or above the heat releasing surface.

9. The chemical heating, volatilizing apparatus according to claim 1, wherein the first mark has a color that indicates the end point, and the second mark has a color representing the start point.

10. The chemical heating, volatilizing apparatus according to claim 9, wherein the color changes occur gradually as a time of heating the chemical containing body elapses.

11. The chemical heating, volatilizing apparatus according to claim 1, wherein the color changes occur gradually as a time of heating the chemical containing body elapses.

12. The chemical heating, volatilizing apparatus according to claim 1, wherein the indicator comprises a laminated film structure, which comprises:
   a color and shade changing layer that retains a color and shade changing substance therein;
   a printed layer, which comprises a transparent film having a thickness of 5 to 30 microns, and which is disposed at a front side of the color and shade changing layer, and
   a base layer, which comprises an opaque film having a thickness of at least 50 microns, and which is disposed at a rear side of the color and shade changing layer.

13. The chemical heating, volatilizing apparatus according to claim 12, wherein the first mark and the second mark are printed on the base layer.

14. The chemical heating, volatilizing apparatus according to claim 13, wherein the color and shade changing layer changes color from a first color at the start point to a second color at the end point, and wherein the first mark is printed in the second color, and the second mark is printed in the first color.

15. The chemical heating, volatilizing apparatus according to claim 14, wherein the base layer is the first color.

16. The chemical heating, volatilizing apparatus according to claim 12, further comprising a covering plate provided at a front side of the printed layer.

17. The chemical heating, volatilizing apparatus according to claim 16, wherein the covering plate has an ultraviolet absorbing agent incorporated therein.

18. The chemical heating, volatilizing apparatus according to claim 1, wherein the indicator is coupled to the chemical containing body retaining receptacle.

* * * * *